United States Patent [19]
Davidson

[11] Patent Number: 5,458,653
[45] Date of Patent: Oct. 17, 1995

[54] PROSTHETIC IMPLANTS WITH BIOABSORBABLE COATINGS

[75] Inventor: James A. Davidson, Germantown, Tenn.

[73] Assignee: Smith & Nephew Richards, Inc., Memphis, Tenn.

[21] Appl. No.: 60,484

[22] Filed: May 11, 1993

Related U.S. Application Data

[63] Continuation of Ser. No. 730,354, Jul. 15, 1991, abandoned.

[51] Int. Cl.⁶ ............................... A61F 2/34; A61F 2/28; A61F 2/30
[52] U.S. Cl. ............................... 623/23; 623/16; 623/18; 623/20
[58] Field of Search ..................... 623/16, 18, 19, 623/20, 22, 23, 66, 11, 12

[56] References Cited

U.S. PATENT DOCUMENTS

| | | | |
|---|---|---|---|
| 4,164,794 | 8/1979 | Spector et al. | 623/23 |
| 4,192,021 | 3/1980 | Deibig . | |
| 4,202,055 | 5/1980 | Reiner et al. . | |
| 4,338,926 | 7/1982 | Kummer et al. . | |
| 4,495,664 | 1/1985 | Blanquaert . | |
| 4,512,038 | 4/1985 | Alexander et al. | 623/16 |
| 4,655,777 | 4/1987 | Dunn et al. | 623/18 |
| 4,713,076 | 12/1987 | Draenert | 623/16 |
| 4,781,183 | 11/1988 | Casey et al. | 623/16 |
| 4,863,475 | 9/1989 | Andersen et al. | 623/66 |
| 5,007,931 | 4/1991 | Smith | 623/23 |
| 5,013,315 | 5/1991 | Barrows | 606/71 |

FOREIGN PATENT DOCUMENTS

| | | |
|---|---|---|
| 0176711 | 9/1986 | European Pat. Off. . |
| 8102668 | 1/1981 | WIPO . |
| 8505027 | 11/1985 | WIPO . |
| WO87/00419 | 1/1987 | WIPO . |
| 9009154 | 8/1990 | WIPO . |
| 9103992 | 4/1991 | WIPO . |

*Primary Examiner*—David Isabella
*Attorney, Agent, or Firm*—Pravel, Hewitt, Kimball & Krieger

[57] ABSTRACT

A novel coated prosthesis that can be tailored to avoid the problem of bone resorption caused by stress shielding. The permanent, load-bearing skeletal replacement prosthesis is coated or covered with a bioabsorbable polymer at selected sites on its surface so that bone affixation is preferentially delayed at these covered sites and bone adjacent to uncoated areas are not stress shielded. Thus, resorption is avoided. When the bioabsorbable polymer is gradually absorbed away, bone affixation takes place on the exposed surfaces, as needed.

27 Claims, 2 Drawing Sheets

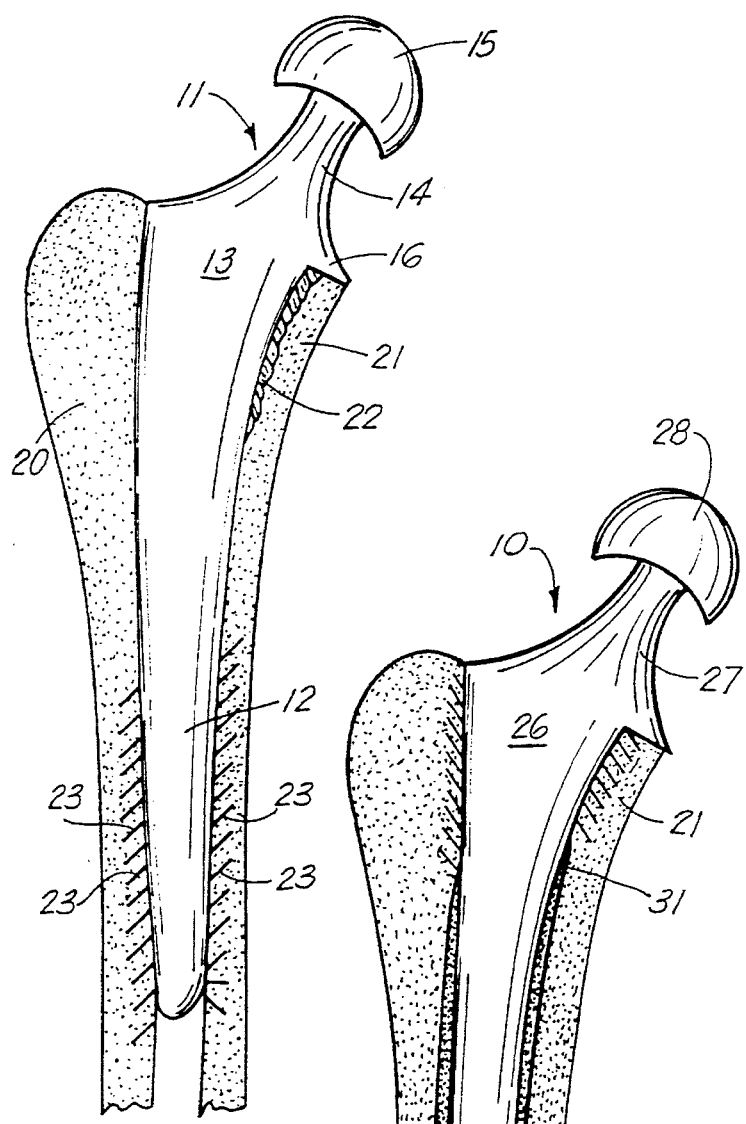
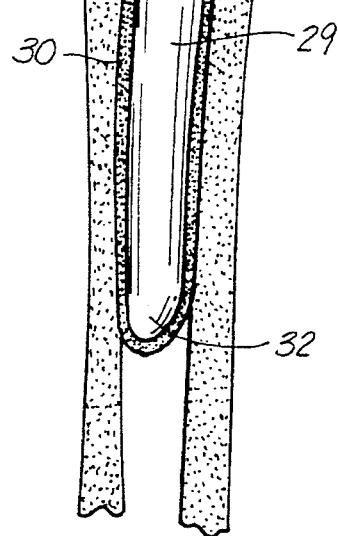
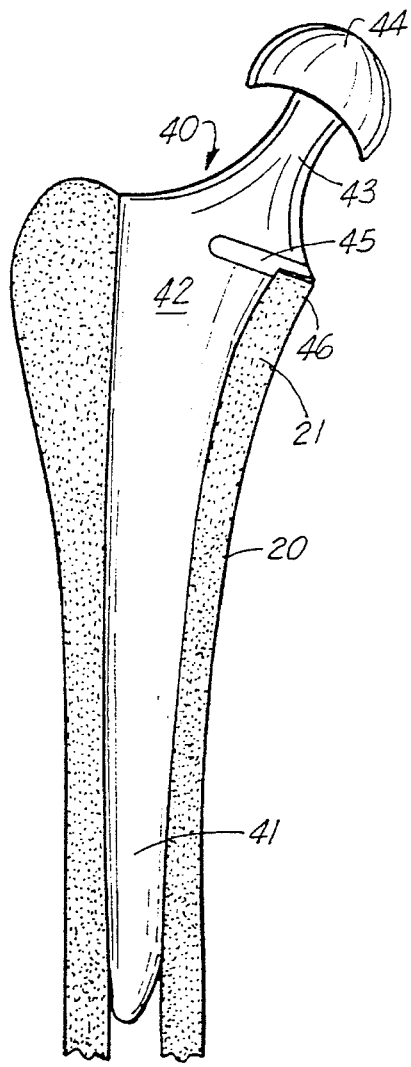
FIG. 1
FIG. 2
FIG. 3

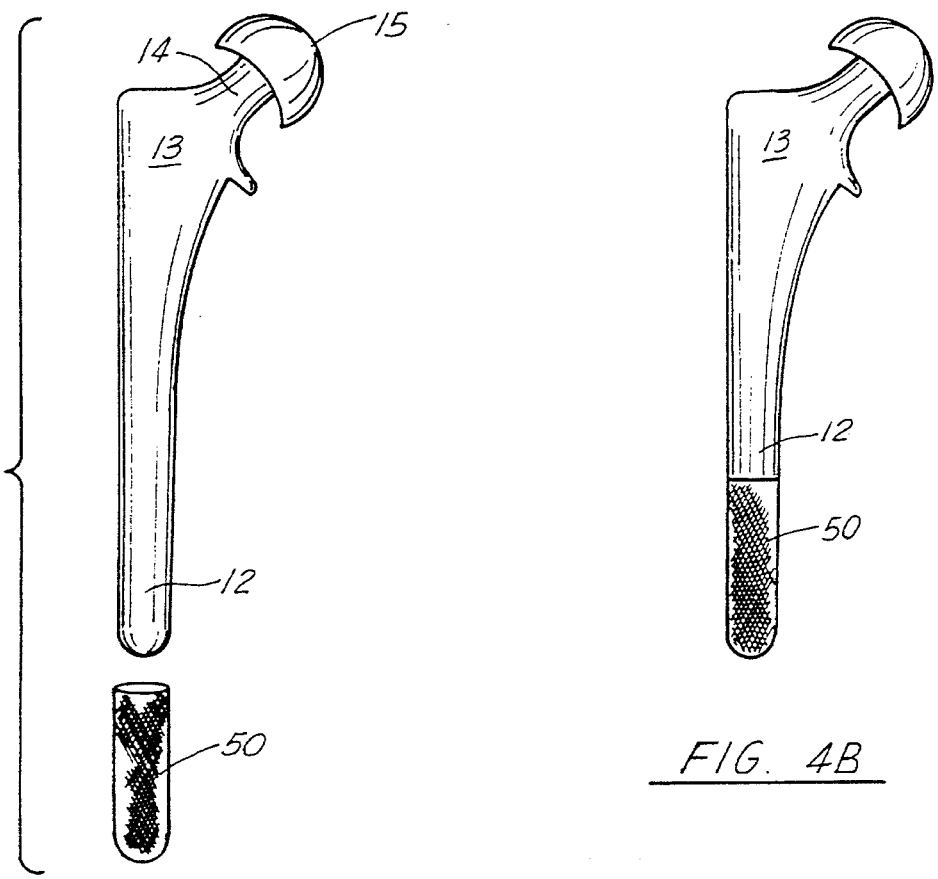
FIG. 4A
FIG. 4B
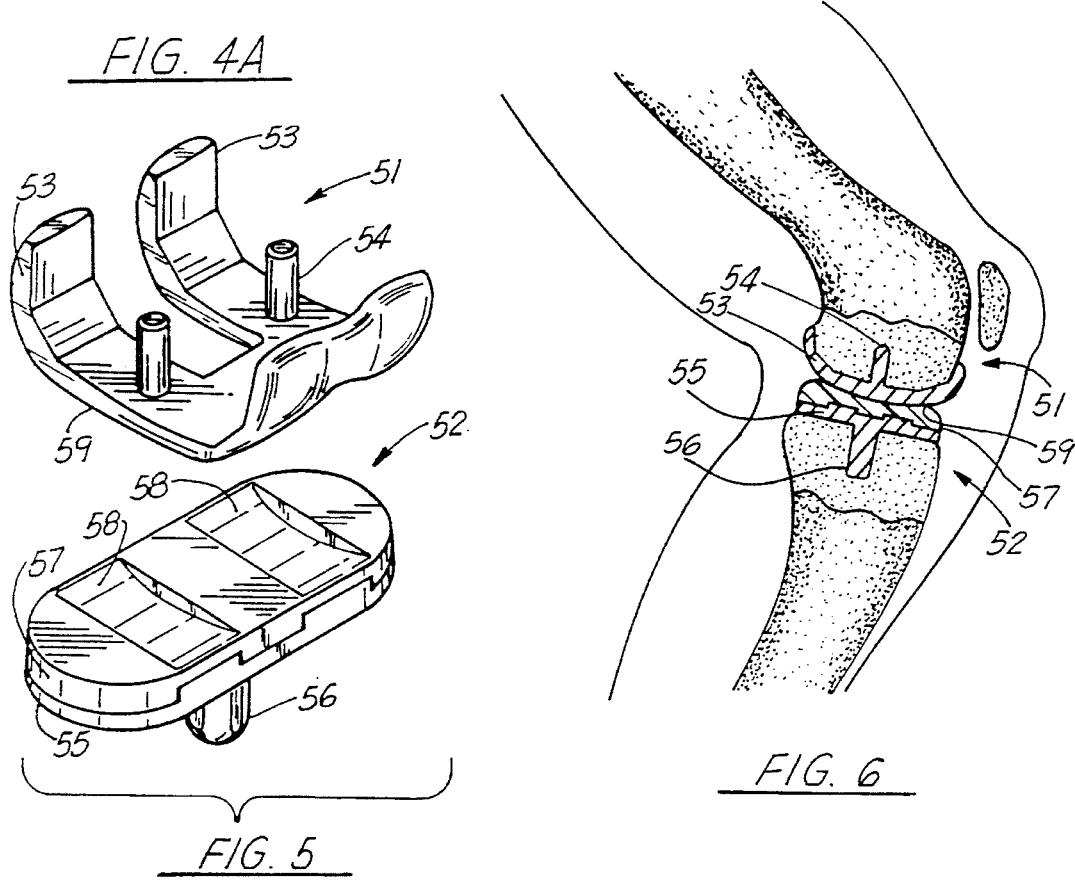
FIG. 5
FIG. 6

PROSTHETIC IMPLANTS WITH BIOABSORBABLE COATINGS

This is a continuation of application Ser. No. 07/730,354 filed on Jul. 15, 1991 now abandoned.

BACKGROUND OF THE INVENTION

1. Field of the Invention

The present invention relates to prosthetic devices, including hip joint stems and knee joint fixation posts, and more particularly to prosthetic devices that are coated or covered by a bioabsorbable material to provide selective stress shielding of or attachment by the adjacent bone while the implant is healing into place.

2. Description of the Related Art

Surgeons believe that distal fixation of a pres-fit (cementless) femoral hip implant can occur too early and thereby create stress shielding in the proximal region of the femur. Fixation posts on the tibial and femoral knee implant can create similar effects. This stress shielding can lead to adverse bone resorption with its attendant adverse effects on the patient. For example, stress shielding causes the bone to retreat (resorb) from its tight fit around a prosthetic implant thereby introducing some "play" into the fit. Depending upon the type of implant, metallic, polymer composite or ceramic, this loosening can lead to wear or microfretting of the implant's surface thereby releasing wear debris into the body tissue. Not only might this wear debris have adverse health consequences for the patient, but this wear debris can lead to accelerated fretting or abrasive wear of the implant thereby aggravating the further loosening of the implant. If unchecked, this situation may ultimately result in a need for major surgery to replace the implant. Such replacement may then necessitate further bone removal to provide a suitable seat for a new implant. The cycle of implantation, bone resorption, implant loosening, and replacement may then recommence. This cycle is clearly harmful to the patient and the bone resorption effect is especially harmful if the patient is young and active since the patient may then need several replacements during his or her lifetime.

Various patents and published patent applications disclose coatings of bioresorbable polymers onto prosthetic bone implants. In some cases, these coatings were on porous surfaces of the prosthesis and were comprised of bioresorbable polymers and tricalcium phosphate which encourages bone ingrowth into the porous surface. In other cases, the bioabsorbable polymer coating is used with an implant for mending fractured bones, such as for example a bone plate. For instance, U.S. Pat. No. 4,338,926 describes a metal implant wherein a biologically absorbable synthetic polymeric coating is held under compression between a bone plate and adjacent fractured bone. The bone plate carries the stress load thereby shielding the bone from stress while the bone fracture is healing. While the fracture heals, gradually reducing the need for stress shielding, the polymeric material is gradually being absorbed into the body. As the absorption of the polymeric material approaches completion, substantially all of the stresses are carried by the healed bone. Thus, bone resorption is avoided. Another embodiment of U.S. Pat. No. 4,338,926 describes an intramedullary rod driven into the medullary canal of a fractured bone. The intramedullary rod is coated with a biologically absorbable material, the coating being in contact with the inner surface of the fractured bone. Again, the rod stress shields the bone fracture while the absorbable coating gradually leaches away transferring load back to the healing bone, but does not relate to controlling bone support of the device.

Significantly, U.S. Pat. No. 4,338,926 is not directed to solving problems of stress shielding and the attendant bone resorption associated with load bearing prostheses intended as a permanent replacement for the skeletal bone, such as hip joint stems, knee prostheses, and the like. The patent only addresses the problem of stress shielding when temporarily supportive implants, such as bone plates and intramedullary pins, are used. These could shield bone from stress to the point that the bone resorbs, becomes thinner, and is subject to greater risk of fracture. These methods do not relate to controlling bone attachment and subsequent support of the implant by the bone.

U.S. Pat. No. 4,990,161 to Kampner addresses the problem of abnormal transference of stress to the more distal areas of the bone shaft in most hip joint implants. Kampner attributes this problem to the penetration of the implant's stem down to the medullary cavity of the bone. Kampner's solution is a stemless implant. Thus, the Kampner patent is directed to an implant with a resorbable stem, i.e. the distal, bioabsorbable region and all key fixation regions, e.g. distal stem tip, screws, and tibial posts are constructed entirely of resorbable material. However, gradual elimination of these fixation areas will lead to micromotion and instability. Thus, the Kampner patent would not provide long term stability. Moreover, the Kampner patent is directed toward the use of a bioabsorbable polymer post or stem. Such polymer stems do not provide as much initial stability as a metal stem. Further, implants having entirely bioabsorbable stems and key fixation areas present the body with a large amount of degradation products the body must metabolize and tolerate.

One patent U.S. Pat. No. 4,888,023 describes an attachable distal sleeve for a total hip made of a polished metal and described as an integral part of the stem. Although the intent is to minimize bone attachment along the side of the sleeve because of the polish, the sleeve is permanent, and will not necessarily eliminate bone support below the distal tip.

In the case of permanent skeletal replacement load bearing implants, a section of the bone-implant interface may carry most of the imposed load while the rest of the adjacent bone is shielded from the load. The stress-shielded bone is subject to the resorption phenomenon, as explained above for the case of hip joints. Often by the very nature and shape of an implant, a certain amount of stress shielding of some adjacent bone is almost inevitable. Therefore, a technique of controlling stress or load shifting over a period of time on selected areas of the affected bone is needed to reduce or eliminate stress-shielding induced bone resorption. Preferably, this technique should not involve subjecting the patient to surgery to correct the stress shielding effect.

SUMMARY OF THE INVENTION

The invention provides loading bearing permanent skeletal replacement prostheses, and methods for making such prostheses, that substantially reduce stress shielding and the attendant bone resorption. The invention prostheses comprise a bioabsorbable coating that covers that portion of the implant which is in contact with the bone area where bone fixation is to be initially retarded. This allows good initial support but preferential bone fixation at other points on the implant's surface in contact with living bone. The bioabsorbable coating is gradually absorbed from the implant's surface and metabolized, exposing surface for later affixation or anchoring in the adjacent bone. The slow absorption rate maintains good support and stability while not allowing direct bonding with the bone until a later time.

To properly counteract stress-shielding, the bioabsorbable coating should be placed on those implant surfaces that will initially bear the highest stress or loading when the implant is in place in an active patient. Thus, for instance, in a hip joint stem, the coating should be on the distal portion of the stem. Further, the thickness of the coating may be varied depending upon the length of time during which the adjacent bone should be retarded from anchoring the implant. Thus, the thickest part of the coating of a hip joint stem may be at the very base of the hip joint stem while the thinnest part may be nearer the proximal end of the stem. Such tailoring of coating thickness should allow preferential bone loading at the point where the uncoated proximal end of the stem abuts against the intramedullary space thereby promoting bone ingrowth in that area. Once the coating is absorbed progressively and gradually from the stem, bone affixation may then progress down the length of the stem to the base of the stem. Additionally, osteoinductive agents such as bone morphogenic proteins, growth factors, etidronates, hydroxyapatite, and other calcium phosphate materials can be incorporated strategically within or beneath the absorbable coating to help further control bone response with time.

The present invention provides an improved hip prosthesis that includes a prosthesis body having an enlarged proximal end portion having a collar and a neck adapted for carrying a femoral head, and a tubular distal stem or shank end portion. A bioabsorbable coating substantially covers the distal stem end portion of the prosthesis body for reducing the tendency of bone attachment at the distal end portion of the prosthesis body. Thus, affixation occurs first at the proximal end of the prosthesis body while the bioabsorbable coating is being gradually dissolved at the distal end portion. This ensures a tight fit of the stem of the prosthesis into the medullary canal of the hip bone, but eliminates early, premature fixation by the bone. In a similar sense, tibial plate and other fixation posts and the anterior and posterior bone interface surfaces of knee prosthesis components may be treated with an absorbable coating.

The coating is a biocompatible bioabsorbable polymer. These polymers are commonly known by those familiar with bioabsorbable and other biodegradable polymers, and include, for example, polylactic acid (PA), polyglycolic acid (PG), PA-PG copolymers, polydioxanone, polycaprolactone, growth factors, bone morphogenic proteins (BMPs), polypeptides, BOP, trimethylene carbonate, hydroxybutyrate polymer, appropriate copolymers of these, and the like. Premolded, thermoformable coatings in the form of slip-on caps from polymers such as co-polymers of lactide and trimethylene carbonate hydroxybutyrate or lactide-polydioxanon can also be used and attached at the time of surgery. The coating may also contain osteogenic materials such as hydroxyapatite and tricalcium phosphate for controlled bone ingrowth into spaces left behind when the polymer is absorbed. Similarly, antibiotics, as well as bone-stimulating drugs to counter osteoporotic bone conditions, such as etidronate or similarly effective drugs, can also be added to the polymer.

The proximal end of the hip stem prosthesis body has, in one embodiment, a collar and the bioabsorbable coating covers at least a portion of that collar. The collar can have a downwardly facing underside surface adapted to register with the top of a patient's femur. The underside of the collar is the surface which is at least partially covered with the bioabsorbable coating.

It is sometimes preferred to implant a hip joint prosthesis without a collar. However, collars are useful at the surgical implantation step because they provide a supportive ridge or rim for ease of implanting the prosthesis and help maintain joint alignment. The invention provides a hip joint stem that has a collar of bioabsorbable polymer that will gradually metabolize away after implantation leaving behind the desired collar-less stem. Thus, the prosthesis provides the benefit of ease and function of implantation of a collared prosthesis while satisfying the need for a collar-less permanent hip joint stem.

Further, for controlled bone growth around the implant, the bioabsorbable polymeric coating may include an osteogenic composition such as hydroxyapatite, tricalcium phosphate, BMP, growth factors, etidronates, and the like. These compositions will remain behind as the bioabsorbable polymer is absorbed thereby leaving an osteoinductive surface for bone attachment. The implant surface may similarly be coated with beads or wire mesh to promote bone ingrowth and anchoring of the implant following resorption of the polymer coating.

Finally, the coating may include a medicament to promote tissue healing and/or reduce inflammation by antibiotic effect. Thus, for instance, the coating may be doped with a therapeutically effective level of antibiotic such as gentamicin, penicillin, cephalosporin and the like, during the absorption of the polymer coating which will leach out at a therapeutically effective rate.

BRIEF DESCRIPTION OF THE DRAWINGS

For a further understanding of the nature and objects of the present invention, reference should be made to the following detailed description, taken in conjunction with the accompanying drawings, in which like parts are given like reference numerals, and wherein:

FIG. 1 is a side view of a prior art type hip prosthesis illustrating early distal fixation;

FIG. 2 is a side elevational view of the preferred embodiment of the apparatus of the present invention illustrating improved proximal fixation first;

FIG. 3 is a side elevational view of a second embodiment of the apparatus of the present invention that includes a collar having a bioresorbable coating layer thereon.

FIGS. 4a and b illustrate the use of a pre-molded thermoformable polymer sleeve which can be warmed and slipped onto the distal part of the hip stem at the time of surgery.

FIG. 7 shows the typical components of a knee prosthesis.

DETAILED DESCRIPTION OF THE PREFERRED EMBODIMENTS

The invention provides novel load-bearing permanent skeletal replacement prostheses that reduce or shift (control) stress-shielding effects on adjacent bone. These orthopedic prosthesis are designed for insertion into any articulating joint space.

Generally, the orthopedic prosthesis is comprised of at least one component of a two-component system wherein the components are interacting and cooperating. When the orthopedic prosthesis comprises one component of a two-component system, the second component is the natural bone. Alternatively, the prosthesis could comprise both components of the two-component system. Under these circumstances, the two components may comprise, for instance, a hip joint stem and an acetabular cup or a tibial plate and femoral component of a knee joint.

The invention prostheses are coated, with a bioabsorbable coating or via a thermoformable cap at the time of surgery, at preselected locations, on their surfaces to initially retard anchoring of the prosthesis in the bone at the selected surface locations. Therefore, in a two-component system, the at least one component will be at least partially coated with the bioabsorbable coating.

The bioabsorbable polymers useful in the invention include those biocompatible polymers and copolymers that will coat the implant material or provide a premolded thermoformable cap or sleeve, that are non-toxic and that can be tailored to degrade or absorb at a preselected rate in the body. These polymers include polylactide (PA), polyglycolide acid (PG), PA-PG copolymer, polypeptides, trimethylene carbonate, hydroxybutyrate, polycaprolactone, polydioxanon, their appropriate copolymers, and the like. The rate of bio-degradation of these polymers and copolymers can be controlled, and vary one from the other. Further, in general, the rate of degradation of a higher molecular weight polymer of any one type will be slower than that of a lower molecular weight polymer. Thus, selection of a polymer of a particular average molecular weight or range of molecular weights, copolymerization, and selection of coating thickness will fix the "life" of the coating. These combinations and absorption or degradation rates can be readily determined by those skilled in the art to enable selection of an appropriate polymer for a specific application. Other factors such as porosity in the polymer, the type of processing or dilution required to attach the coating, and the stress experienced by the polymer during implantation can alter absorption or degradation rate. Furthermore, the addition of antibiotics and osteogenic agents will alter this absorption rate. Specific absorption rates will depend on these factors and can be determined for a specific need or application, or coating method.

FIG. 1 shows a prior art type prosthesis 11 having a lower, generally cylindrical or tubular stem or shank portion 12, and an upper enlarged midportion 13 equipped with a neck 14 region and a femoral head 15. The head 15 can be integrally connected to neck 14 or may be removably affixed thereto. A collar 16 with an underside shoulder surface 17 extends outwardly of the prosthesis body midportion 13.

In FIG. 1, the prosthesis body is a hip joint prosthesis occupying the femur 20 with a shoulder 17 resting upon the proximal or upper end 21 thereof. A calcar region 22 is shown in FIG. 1 and early distal fixation is indicated at 23 as occurring in the area of the generally cylindrical stem 12. This early distal fixation 23 transfers load to this region thereby shielding the bone in contact with the proximal region of the stem 13 from stresses. This reduces the ability of the proximal stem 13 to properly load and transfer stress to the calcar, thus bone resorption can and frequently does occur in this region.

In FIG. 2, a preferred embodiment of the apparatus of the present invention is shown, generally designated by the numeral 10. Prosthesis 10 includes a prosthesis body 25 having a midportion 26, a neck region 27, a femoral head 28 and a lower, generally cylindrical stem 29. A bioabsorbable coating 30 extends over the cylindrical stem, beginning at a the location point 31 just below the midsection 26, and extending downwardly to the lowermost tip 32 of the cylindrical stem 29, as shown in FIG. 2.

The coating 30 controls the areas of the implant 10 that will be supported by the bone both initially and in the and longer term to ensure optimum load transfer over a period of time. The bioresorbable coating 30, such as polylactic acid, placed on the distal region 29 of the hip stem shown in FIG. 2, will temporarily shield the distal region from becoming affixed to the bone. This will result in bone support initiating at the proximal 21 region of the femur 20, as desired. Later, when the coating 30 at the distal end 29 of the prosthesis body 25 has substantially resorbed, bone growth will support this region as well as needed.

FIG. 3 shows a collared prosthesis 40 that includes a lower, rounded stem 41, a midsection 42, a neck region 43, and an acetabular head 44. A collar 45 extends from the midsection 42 and is provided with a coating 46 of bioabsorbable material, preferably on the underside of the collar 45. Thus, the prosthesis provides a surface of bioabsorbable material that interfaces with the proximal end of the femur 21, as shown in FIG. 3.

A collar is sometimes used with a hip joint prosthesis for assuring a proper joint alignment during surgery and to avoid subsidence. The resorbable coating 46 can be applied to the surface under the collar 45 (FIG. 3). This will ensure proper press fit condition at surgery and resistance to subsidence. The coating will, however, later resorb at a predetermined rate and at a predetermined time once the prosthesis body 40 and stem 41 have been stabilized by new, remodeled bone.

The above technique is also useful in carbon fiber polymer composite hip stems equipped with collars. In that case it may be undesirable, from a composite strength standpoint (long term), to have excessive loading of the collar by the proximal-medial femoral cortex. Placement of a resorbable coating under the collar will provide initial support when the patient is recovering (and when hip loads are relatively low). Once the stem has been stabilized by new remodeled bone, the coating would resorb and the loading on the distal end of the stem would reduce and eventually eliminate the loading against the collar in the longer term.

To accommodate surgeons who prefer uncollared stems, a modular collar could readily be incorporated to provide an option at the time of surgery. The removable collar 45 could be slidably mounted upon a slot in the proximal area and would thus be selectively attachable to the prosthesis body 40.

FIGS. 4a and b illustrate the use of a thermoformable premolded bioabsorbable cap or sheath 50. This cap or sheath is premolded to fit snugly over, for example as illustrated, the distal end of a hip stem. The premolded cap is desirably of slightly smaller dimension than the shape over which it is intended to fit. The cap is then heated to a point where it becomes pliable and may be manipulated and stretched to fit over the surface to be covered. Upon cooling, the cap shrinks slightly to form a tightly fitting coating.

A typical knee joint prosthesis is shown in FIG. 7. The knee joint includes a femoral component 20 and a tibial component 30. The femoral component includes condyles 22 which provide the articulating surface of the femoral component and pegs 24 for affixing the femoral component to the femur. The tibial component 30 includes a tibial base 32 with a peg 34 for mounting the tibial base onto the tibia. The tibial platform 36 is mounted atop the tibial base 32 and is supplied with grooves 38 similar to the shape of the condyles 22. The bottom surfaces of the condyles 26 contact the tibial platform's grooves 38 so that the condyles articulate within these grooves against the tibial platform. While condyles are typically fabricated of metals, the tibial platform may be made from an organic polymer or a polymer-based composite. As in the case of the hip joint, porous bead or wire mesh coatings can also be applied to either the tibial or femoral components of the knee or both. Thus, the knee joint prosthesis of the present invention comprises a prosthesis comprises a prosthesis body having a proximal and distal stem end portions. The bioabsorbable coating substantially covers the distal stem end portion. The presence of the coating delays initially the bone attachment at the coated distal end portion so that affixation occurs first at the proximal end of the prosthesis body.

Upon reading the above disclosure, changes and modifications may occur to one of skill in the art. Such changes and modifications are within the scope and spirit of the invention as described above and claimed herebelow.

I claim:

1. An orthopedic prosthesis for insertion into an articulating joint space comprising:
   a) at least one component of a two-component joint system wherein each of said components are equipped with outer surfaces that cooperate with surfaces of the other component, the at least one component having surfaces that, upon initial implantation of said component, will be in contact with bone; and
   b) a bioabsorbable coating covering surface areas of the at least one component that will be in contact with the bone initially to provide load transfer over time from implant to bone by initially delaying bone attachment at the coated surfaces so that bone affixation occurs first at any uncoated surfaces of the prosthesis.

2. The orthopedic prosthesis of claim 1 wherein said bioabsorbable coating comprises a bioabsorbable polymer.

3. The orthopedic prosthesis of claim 1 wherein said at least one component of the prosthesis comprises a bone tissue ingrowth receptive outer surface covered by said bioabsorbable coating.

4. The orthopedic prosthesis of claim 2 wherein said bioabsorbable polymer is a polymer selected from the group consisting of polylactide, polyglycolide, polydioxanone, polycaprolactone, hydroxybutyrate, and their copolymers.

5. The orthopedic prosthesis of claim 4, wherein a composition selected from the group consisting of osteogenic agents, bone morphogenic proteins, growth factors, antibiotics, anti-osteoporotics, and anti-inflammatory substances is incorporated within or beneath the bioabsorbable coating to control bone response with time.

6. The orthopedic prosthesis of claim 2 wherein the at least one component of the prosthesis outer surface is comprised of a material selected from the group consisting of a metal alloy, a ceramic, and an organic polymer composite.

7. The orthopedic prosthesis of claim 3 wherein the ingrowth receptive outer surface comprises beads or a mesh and the bioabsorbable coating is a polymer selected from the group consisting of polylactide, polyglycolide, polydioxanone, polycaprolactone, hydroxybutyrate, and their copolymers.

8. The orthopedic prosthesis of claim 7, wherein a composition selected from the group consisting of osteogenic agents, bone morphogenic proteins, growth factors, antibiotics, anti-osteoporotics, and anti-inflammatory substances is incorporated within or beneath the bioabsorbable coating to control bone response with time.

9. The orthopedic prosthesis of claim 1 wherein the bioabsorbable coating is a sheath comprising a thermoplastic, biocompatible polymer; said sheath covering at least a portion of the surface of said orthopedic prosthesis and firmly attached to the surface portion.

10. A hip prosthesis comprising:
    a) a prosthesis body having proximal and distal portions with outer surfaces; and
    b) a bioabsorbable coating at least partially covering the outer surface of the distal portion for initially delaying bone attachment at the coated surfaces so that bone affixation occurs first at any uncoated surfaces of the prosthesis body.

11. The hip prosthesis of claim 10 wherein said bioabsorbable coating comprises a bioabsorbable polymer.

12. The hip prosthesis of claim 10 wherein said prosthesis comprises a bone tissue ingrowth receptive outer surface covered by said bioabsorbable coating.

13. The hip prosthesis of claim 11 wherein said bioabsorbable polymer is a polymer selected from the group consisting of polylactide, polyglycolide, polydioxanone, polycaprolactone, hydroxybutyrate, and their copolymers.

14. The hip prosthesis of claim 13, wherein the coating further comprises a composition selected from the group consisting of osteogenic agents, bone morphogenic proteins, growth factors, antibiotics, anti-osteoporotics, and anti-inflammatory substances.

15. The hip prosthesis of claim 11 wherein the proximal end of the prosthesis body comprises a collar and the bioabsorbable coating covers at least part of the collar.

16. The hip prosthesis of claim 15 wherein the collar is comprised of a bioabsorbable polymer.

17. The hip prosthesis of claim 12 wherein the ingrowth receptive outer surface comprises beads or a mesh and the bioabsorbable coating is a polymer selected from the group consisting of polylactide, polyglycolide, polydioxanone, polycaprolactone, hydroxybutyrate, and their copolymers.

18. The hip prosthesis of claim 17, wherein a composition selected from the group consisting of osteogenic agents, bone morphogenic proteins, growth factors, antibiotics, anti-osteoporotics, and anti-inflammatory substances is incorporated within or beneath the bioabsorbable coating to control bone response with time.

19. The hip prosthesis of claim 10 wherein the bioabsorbable coating is a sheath comprising a thermoplastic, biocompatible polymer; said sheath covering at least a portion of the surface of said hip prosthesis and firmly attached to the surface portion.

20. A knee joint prosthesis comprising:
    a) a prosthesis having a femoral component with a first distal portion, and a tibial component with a second distal portion;
    b) a bioabsorbable coating, at least substantially covering the first and second distal portions of the prosthesis, for delaying initially bone attachment at the coated distal portions of the prosthesis so that affixation occurs first at proximal bone-contacting portions of the prosthesis while the bioabsorbable coating is gradually dissolved at said distal portions.

21. The knee prosthesis of claim 20 wherein said coating comprises polylactide, polyglycolide, polydioxanone, polycaprolactone, hydroxybutyrate, and their copolymers.

22. The knee prosthesis of claim 21, wherein a composition selected from the group consisting of osteogenic agents, bone morphogenic proteins, growth factors, antibiotics, anti-osteoporotics, and anti-inflammatory substances is incorporated within or beneath the bioabsorbable coating to control bone response with time.

23. The knee prosthesis of claim 21, wherein said coating is on a fixation post of any other total joint replacement component.

24. The knee prosthesis of claim 23, wherein said fixation post is a tibial post.

25. The knee prosthesis of claim 21, wherein said coating is a pre-molded sheath.

26. The knee prosthesis of claim 25, wherein said bioabsorbable polymer coating was thermally transformed to allow said coating to be slipped onto the tibial post.

27. The orthopedic prosthesis of claim 20, wherein the bioabsorbable coating comprises a bioabsorbable polymer.

* * * * *